United States Patent
Vanden Berghe

(12) 
(10) Patent No.: US 6,495,531 B2
(45) Date of Patent: *Dec. 17, 2002

(54) USE OF GLUCOSAMINE AND GLUCOSAMINE DERIVATIVES FOR QUICK ALLEVIATION OF ITCHING OR LOCALIZED PAIN

(75) Inventor: Dirk Andre Richard Vanden Berghe, Laarne (BE)

(73) Assignee: New Key Foods N. V., Knokke (BE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/214,455

(22) PCT Filed: May 22, 1998

(86) PCT No.: PCT/EP98/03175

§ 371 (c)(1), (2), (4) Date: Oct. 1, 1999

(87) PCT Pub. No.: WO98/52576

PCT Pub. Date: Nov. 26, 1998

(65) Prior Publication Data

US 2001/0053771 A1 Dec. 20, 2001

(30) Foreign Application Priority Data

May 21, 1997 (EP) .............................. 97201513

(51) Int. Cl.⁷ .............................. A61K 31/70
(52) U.S. Cl. ....................................... 514/62
(58) Field of Search ................ 514/460, 459, 514/62

(56) References Cited

U.S. PATENT DOCUMENTS 4,772,591 A  9/1988  Meisner

FOREIGN PATENT DOCUMENTS

EP  0281812  9/1988
JP  04054126  * 2/1992

OTHER PUBLICATIONS

Schultz et al, Hyaluronates for the treatment of pain . . . , Database CAPLUS, AN 1988:161432, abstract of patent (e.g. US 4808576).*
Aasakura, H. et al., Nippon–Naika—Gekki—Zasshi, 84(11):1815–20 (1995).
Delgadillo, R.A. et al., J. Pharm. Pharmacol 40:488–493 (1988).
Dragani, L. et al., Minerva Med. 80(4):397–403 (1989).
Dragani, L. et al., Riv. Fur. Sci. Med. Pharmacol. 12:283–295 (1990).
McCarty, M.F., Med. Hypotheses 42 (5):323–327 (1994).
McCarty, M.F., Med. Hypotheses 47(4):273–275 (1996).
Reichelt, A. et al., Arzneimittel Forschung 44(1):75–80 (1994).
Schmidt, R.J. et al., J. Pharm. Pharmacol 41:784 (1989).
Setnikar, I., Int. J. Tissue–React. 14(5):253–261 (1992).
Spencer–Green, G., 1Postgrad. Med. 93(7):129–140 (1993).
Talent, J.M. et al., Clin. Ther. 18(6):1184–1190 (1996).
Patent Abstracts of Japan; Mori; JP 04 054126 A; Feb. 21, 1992.

* cited by examiner

Primary Examiner—William R. A. Jarvis
Assistant Examiner—Vickie Kim
(74) Attorney, Agent, or Firm—Webb Ziesenheim Logsdon Orkin & Hanson, P.C.

(57) ABSTRACT

The present invention relates to the new use of glucosamine and/or its derivatives for the preparation of a therapeutical composition for treating and quick relief of itching and/or local pain which results from a variety of causes. The invention further relates to therapeutical compositions for use in this treatment.

4 Claims, No Drawings

USE OF GLUCOSAMINE AND GLUCOSAMINE DERIVATIVES FOR QUICK ALLEVIATION OF ITCHING OR LOCALIZED PAIN

This application is a 371 of PCT/EP98/03175 filed May 22, 1998.

FIELD OF INVENTION

The invention relates to the preparation of a topical medication for very quick alleviation and relief of itching and/or localized pain caused by a wide range of medical indications.

BACKGROUND OF THE INVENTION

Itching (pruritus) has a lot of underlying causes and can lead to a lot of complications by scratching. Itching may be associated with local pain. Pain can also occur independently. Both local pain and itching comprise the sensation associated with a lot of causes: inflammation, dry skin, infection by micro-organisms such as bacteria, fungi and viruses, corns, wounds, ulcers, stings, insect bites, allergic reactions, hyper proliferation of the epithelial layer, different types of treatment with chemicals, affecting the skin, eczema, etc. But there is also local pain associated with other affections, such as tendinitis, rheumatism and rheumatic affections, such as reumatalgia, reumatide reumatismus articulorum acutus, reumatismus articulorum chronicus, reumatismus musculorum, reumatismus nervosum, reumatismus nodosum, rheumatoid affections, different kinds of arthritis such as arthritis urica, arthritis acuta, arthritis sicca, arthritis hyperthrophica, arthritis infectiosa, arthritis rheumatica, different forms of arthrosis, skin burning by sun, other irradiations, chemicals or heat sources.

In all these and other cases pain and/or itching may very often be difficult to treat. Moreover, oral pain killers may have undesired side effects due to their systemic mode of action, especially when taken over a prolonged period of time. Itching in itself can be very inconvenient and scratching can deteriorate the condition.

It is therefore desirable and thus the object of the invention to provide a means for topically treating itching and local pain.

This object was achieved according to the invention when it was found that glucosamine and derivatives thereof when applied topically are capable of controlling, reducing and also inhibiting the initiation of itching and pain caused by a whole range of unrelated conditions.

The medicinal capacity of glucosamine after oral ingestion thereof in a limited number of diseases has been described in the literature. A pilot study of the oral use of N-acetyl-D-glucosamine as a potential treatment for patients with osteoarthritis was published by Talent & Gracy (1996). The potential use of oral glucosamine for wound healing and treatment for osteoarthritis is discussed by McCarty (1994 and 1996). The use of glucosamine in non-specific inflammatory bowel diseases is documented by Aasakura et al. (1995). Reichelt et al. (1994) demonstrated the efficacy and safety of intramuscular glucosamine sulfate in osteoarthritis of the knee.

The use of glucosamine as non steroidal anti-inflammatory drug in reducing the signs and symptoms of osteoarthritis and rheumatoid arthritis is documented by Spencer-Green (1993) and Setnikar (1992). The toxicity of glucosamine for tissue culture cells and the antiviral activity of glucosamine depending on the cell-type and cell-line were demonstrated by Schmidt et al. (1989) and Delgadillo & Vanden Berghe (1988).

More complicated glucosamine compounds were evaluated for use in patients with osteoarthritis of the knee. In the study by Dragani et al. (1989, 1990) heparin-glucoronil glucosaminoglycan was used in a long-term study for 30 days in a 3 daily administration of the drug.

All of these prior art documents are however concerned with oral intake of glucosamine or a derivative thereof. Based on this systemic mode of action it could not be expected that topical application of the compound and/or its derivative(s) could have an alleviating effect on itching and pain.

SUMMARY OF THE INVENTION

The present invention provides for the use of glucosamine and/or its derivatives for the preparation of a therapeutical composition for the topical treatment of itching and/or pain. The effect of the mediation is an acupuncture-like effect, i.e. resulting in a very quick pain reduction.

The invention thus provides topical medicaments for the alleviation of itching and pain. It has surprisingly been found that this alleviation can already take place in a very short delay of time (<1 minute) by single topical treatment. The use of glucosamine or glucosamine derivatives for the topical treatment of indications involving pain and/or itching were never described before. It is also totally new and unexpected that water-soluble compounds, such as glucosamine or glucosamine derivatives, are at all able to penetrate the skin or mucosa and act so quickly on neurons and nerve impulses causing the sensation of irritation and pain. The effect is therefore called: an acupuncture-like effect.

DISCLOSURE OF THE INVENTION

The use according to the present invention requires glucosamine and/or one or more monomeric glucosamine derivatives such as:

D-glucosamine hydrochloride
D-glucosamine sulfate
D-glucosamine iodide or other salts of D-glucosamine
N-acetyl D-glucosamine and their salts
Chitin hydrolysate
Chitosane hydrolysate
Glucosamine phosphates, sulfates, or acetates and their salts
D-glucosaminic acid
N-acetyl D-glucosamine phosphates, sulfates and their salts Hydrolysates of chitin and chitosane can be obtained by chitinase.

The compounds mentioned here are preferably comprised in the therapeutical compositions (also referred to herein as "topical medicament") of the invention in a concentration from 0.1% to 15% (w/w), most preferably from 1% to 10% (w/w).

Topical medicaments prepared according to the invention may further comprise other active compounds for healing diseases that are accompanied by local itching or pain, such as disinfectants, antibiotics, antifungal compounds, wound healing compounds, cosmetic compounds improving the skin conditions, anti-inflammatory compounds, anti-allergic compounds, anti-rheumatic compounds, anti-arthritic compounds, other pain or itching relieving compounds, etc.

According to the invention it has been found that the itching or local pain is completely removed or significantly reduced in a short delay of time of even less than 1 minute for a significant period of at least more than 1 hour considered that appropriate concentrations of the drug are used. Appropriate concentrations comprise more than about 0.1% (w/w) glucosamine compound per gram cream, gel, ointment, solution, etc..

All topical medicaments, prepared according to the invention, may be prepared in any conventional form or in other forms suitable for topical use on the skin or mucous membranes. These forms also include all forms with sustained release compositions or pre-dispersed plasters and other forms containing an acceptable carrier for the compounds.

Cosmetic acceptable carriers and additives may include: forms of vaseline, oils, emollients, surfactants, humefactants, powders, water, preservatives, agents increasing the viscosity such as polysaccharides, polypeptides, fragrances, anti-foam agents, opacifiers, colorants, each in their amount to accomplish their typical function. The basic compositions of the various topical application forms described here are well within the reach of the skilled person.

The present invention will be further illustrated in the following examples, which are in no way intended to be limiting to the invention.

EXAMPLES

Formulation

Glucosamine or one or more of its derivatives was added in the appropriate amount to one of the following formulations. The compositions thus obtained were tested as described in the Examples. All percentages are by weight (w/w) unless otherwise indicated.

Formulation 1
Water

| Formulation 2 | |
| --- | --- |
| Cutina MD ™ | 4% (Henkel, Germany) |
| Lanette N ™ | 3% (Henkel, Germany) |
| Isopropylmyristate | 3% (Henkel, Germany) |
| Oleum Amygdalae | 4% Ph. Eu II (Conforma, Belgium) |
| Glycerol | 5% Ph. EU II (Conforma, Belgium) |
| Methylparahydroxybenzoate | 0.2% |
| Propylparahydroxybenzoate | 0.02% |
| Aqua destillata | ad 100 |

| Formulation 3 | |
| --- | --- |
| Lanette O ™ | 8% (Henkel, Germany) |
| Emulgin B2-C1000 ™ | 4% (Henkel, Germany) |
| Oleum Amygdalae | 5% Ph. Eu II (Conforma, Belgium) |
| Lanette 16 ™ | 2% (Henkel, Germany) |
| Glycerol | 6% Ph. Eu II (Conforma, Belgium) |
| Methylparahydroxybenzoate | 0.2% |
| Propylparahydroxybenzoate | 0.02% |
| Aqua destillata | ad 100 |

Example 1

A patient (female; 52 years) suffering from sore throat caused by β-hemolytic streptococci was treated with a water solution (formulation 1) of N-acetyl-glucosamine (8% w/w). The solution was sprayed into the mouth during 10 seconds in order to treat the infected area. Pain relief occurred already 20 seconds after application and lasted for at least 1.5 hour.

12 hours later the same patient was treated with spray containing glucosamine HCl (9% w/w and 20% glycerol and 10% alcohol in water). Pain relief occurred again very quickly, 36 seconds after application and lasted for at least 2 hours.

Example 2

A patient (male; 42 years) suffering from tendinitis caused by practicing tennis was treated with formulation 2 containing glucosamine sulphate 5% (w/w). The cream was normally applied on the skin during 2 minutes to allow the penetration. Pain relief occurred already after 50 seconds and lasted for at least 2 hours. After 12 hours the same patient was treated with formulation 2 without glucosamine. There was no pain relief after similar application.

Example 3

A patient (female; 53 years) suffering from herpes simplex type I infection around the nose showing extensive fissures was treated with formulation 3 containing 3% glucosamine sulfate (w/w). Already after 30 seconds pain and itching relief occurred and lasted during 3 hours. Remarkably, most of the fissures were closed after 5 hours.

Example 4

A patient (female; 53 years) suffering from pain in the knee caused by a light collision during a car accident was treated with formulation 3 containing 10% (w/w) glucosamine sulfate. Pain relief occurred after 50 seconds and lasted during 3 hours. After 3 new successive treatments every 4 hours the pain was completely gone.

Example 5

A child (male; 8 months) suffering from diaper allergy was treated with composition 2 containing 5% (w/w) glucosamine HCl instead of other commonly used oils. After applications for 1 week (3 times a day) there was always immediate relief of itching and pains.

Example 6

A patient (female; 51 years) with a tendinitis due to the practice of bowling sport was treated 2 days after the onset of pain with composition 3 containing 6% (w/w) N-acetyl D-glucosamine. Pain relief occurred 25 seconds later. After 5 successive treatments (every 2 hours) pain was completely reduced.

Example 7

A patient with allergy for cats (male; 30 years) was confronted with a stroked cat (2 years old) in a closed room (6 m×4 m×3 m) during 10 minutes. 8 minutes later itching started all over the forehead and progressed after 15 minutes to the nose (external x internal).

The patient was treated on the left side of the forehead with composition 3 and on the right side of the forehead with composition 3 containing 5% (w/w) glucosamine HCl. Itching completely disappeared after 45 seconds on the right side while there was still itching on the left side. The nose was also treated inside and outside with the active cream. Itching decreased drastically already after 50 seconds.

Example 8

A patient (male; 17 years) with nettle rash on both hands, 10 minutes after contact with the nettle plants, was treated with composition 3 containing 6% (w/w) glucosamine sulfate on the left hand and composition 3 on the right hand.

Two seconds later the itching was drastically reduced on the left hand while no relief occurred on the right hand.

Example 9

A patient (male; 52 years) suffering from arthritis urica, and not taking any medication, was treated with composition 2 containing 9% (w/w) glucosamine HCl all over the affected right foot by 4 successive treatments with an interval of 10 minutes. Gradually strong pain relief occurred and lasted for 4 hours.

Example 10

A patient suffering from eczema (atopical) (male; 14 years) on the arm-bends was treated with composition 3 containing 8% (w/w) glucosamine HCl on the left arm and composition 3 on the right arm.

Itching decreased drastically after 15 seconds and lasted during 2 hours only on the left arm. From the above it follows that the therapeutical compositions of the invention can be used to alleviate itching and pain which result from a variety of causes. The relief is obtained very quickly and lasts for a considerable period of time.

REFERENCES

Aasakura, H. et al., Nippon-Naika-Gekki-Zasshi 84(11):1815–20 (1995)
Delgadillo, R. A. & Vanden Berghe, D. A., J. Pharm. Pharmacol 40:488–493 (1988)
Dragani, L. et al., Minerva Med. 80(4):397–403 (1989)
Dragani, L. et al., Riv. Fur. Sci. Med. Farmacol. 12:283–295 (1990)
McCarty, M. F., Med. Hypotheses 42(5):323–327 (1994)
McCarty, M. F., Med. Hypotheses 47(4):273–275 (1996)
Reichelt, A. et al., Arzneimittel Forschung 44(1):75–80 (1994)
Schmidt, R. J. et al. J. Pharm. Pharmacol 41:784–784 (1989)
Setnikar, I., Int. J. Tissue-React. 14(5):253–261 (1992)
Spencer-Green, G., Postgrad. Med. 93(7):129–140 (1993)
Talent, J. M. & Gracy, R. W., Clin. Ther. 18(6:1184–1190 (1996)

What is claimed is:

1. A method for the quick relief of itching and/or pain, comprising applying an effective amount of glucosamine and/or one or more of its derivatives to the skin of an animal or human in need of such topical treatment, thereby already significantly reducing itching and/or pain in less than one minute.

2. The method according to claim 1, wherein said effective amount of glucosamine and/or one or more of its derivatives is selected from the group consisting of salts of D-glucosamine, in particular D-glucosamine hydrochloride, D-glucosamine sulfate, D-glucosamine iodide; N-acetyl D-glucosamine and its salts; chitin hydrolysate; chitosane hydrolysate; glucosamine phosphates, sulfates, or acetates and their salts; D-glucosaminic acid; N-acetyl D-glucosamine phosphates, sulfates and their salts.

3. The method according to claim 1 wherein said effective amount of glucosamine is admixed, prior to its application to the skin, with at least one additional therapeutical compound for further treating the medical condition associated with said need for topical treatment.

4. The method according to claim 3 wherein said at least one additional therapeutical compound is selected from the group consisting of disinfectants, antibiotics, antifungal compounds, wound healing compounds, cosmetic compounds improving the skin conditions, anti-inflammatory compounds, anti-allergic compounds, anti-rheumatic compounds, anti-arthritic compounds, anti-blood coagulant compounds, other pain or itching relieving compounds.

* * * * *

UNITED STATES PATENT AND TRADEMARK OFFICE
CERTIFICATE OF CORRECTION

PATENT NO.    : 6,495,531 B2
DATED         : December 17, 2002
INVENTOR(S)   : Dirk A.R. Vanden Berghe It is certified that error appears in the above-identified patent and that said Letters Patent is hereby corrected as shown below:

<u>Title page,</u>
Item [56], References Cited, OTHER PUBLICATIONS, insert:
-- Webster Dictionary, 10$^{th}$ edition, page 598* --.

Signed and Sealed this

Twenty-fourth Day of June, 2003

JAMES E. ROGAN
*Director of the United States Patent and Trademark Office*